(12) United States Patent
Kishima

(10) Patent No.: US 9,029,803 B2
(45) Date of Patent: May 12, 2015

(54) FLUORESCENT-IMAGE ACQUISITION APPARATUS, FLUORESCENT-IMAGE ACQUISITION METHOD AND FLUORESCENT-IMAGE ACQUISITION PROGRAM

(75) Inventor: Koichiro Kishima, Kanagawa (JP)

(73) Assignee: Sony Corporation, Tokyo (JP)

( * ) Notice: Subject to any disclaimer, the term of this patent is extended or adjusted under 35 U.S.C. 154(b) by 3 days.

(21) Appl. No.: 12/825,969

(22) Filed: Jun. 29, 2010

(65) Prior Publication Data

US 2011/0006220 A1   Jan. 13, 2011

(30) Foreign Application Priority Data

Jul. 10, 2009   (JP) ................ P2009-163775

(51) Int. Cl.
*G01J 1/58* (2006.01)
*G01N 21/64* (2006.01)
*G01N 15/14* (2006.01)
*G02B 21/16* (2006.01)
*G06K 9/00* (2006.01)
*G06T 5/00* (2006.01)
*G06T 5/50* (2006.01)
*G06T 7/00* (2006.01)
*H04N 5/76* (2006.01)
*G01N 21/17* (2006.01)
*G01N 21/88* (2006.01)
*H04N 5/781* (2006.01)
*H04N 9/82* (2006.01)

(52) U.S. Cl.
CPC ........ *G01N 21/6458* (2013.01); *G01N 15/1434* (2013.01); *G01N 15/1475* (2013.01); *G01N 21/6428* (2013.01); *G01N 2015/1452* (2013.01); *G01N 2021/1782* (2013.01); *G01N 2021/8822* (2013.01); *G02B 21/16* (2013.01); *G06K 9/0014* (2013.01); *G06T 5/003* (2013.01); *G06T 5/50* (2013.01); *G06T 7/0012* (2013.01); *G06T 2207/10056* (2013.01); *G06T 2207/10064* (2013.01); *G06T 2207/30024* (2013.01); *H04N 5/76* (2013.01); *H04N 5/781* (2013.01); *H04N 9/8205* (2013.01)

(58) Field of Classification Search
USPC .................... 250/459.1, 458.1, 216
See application file for complete search history.

(56) References Cited

U.S. PATENT DOCUMENTS 6,650,357 B1 * 11/2003 Richardson ............. 348/80
6,961,080 B2 * 11/2005 Richardson ............. 348/80

(Continued)

FOREIGN PATENT DOCUMENTS

EP    1785761 A1    5/2007
JP    01-309478    12/1989

(Continued)

OTHER PUBLICATIONS

Partial European Search Report dated Sep. 20, 2010 corresponding to European Patent Appln. No. 10167933.

(Continued)

*Primary Examiner* — David Porta
*Assistant Examiner* — Djura Malevic
(74) *Attorney, Agent, or Firm* — K&L Gates LLP

(57) ABSTRACT

Disclosed herein is a fluorescent-image acquisition apparatus including an excitement-light source; an objective lens; an image pickup device; focal-point movement control means; and image-pickup control means.

9 Claims, 9 Drawing Sheets

(56) References Cited

U.S. PATENT DOCUMENTS

| | | | |
|---|---|---|---|
| 2001/0041347 A1 | 11/2001 | Sammak et al. | |
| 2004/0008867 A1* | 1/2004 | Fein et al. | 382/100 |
| 2005/0121596 A1* | 6/2005 | Kam et al. | 250/201.2 |
| 2005/0211874 A1 | 9/2005 | Takeyama et al. | |
| 2005/0237605 A1* | 10/2005 | Vodyanoy et al. | 359/385 |
| 2005/0277186 A1* | 12/2005 | Fein et al. | 435/288.7 |
| 2006/0050146 A1 | 3/2006 | Richardson | |
| 2008/0107330 A1 | 5/2008 | Cotman et al. | |
| 2009/0086314 A1* | 4/2009 | Namba et al. | 359/383 |

FOREIGN PATENT DOCUMENTS

| | | |
|---|---|---|
| JP | 08-507678 | 8/1996 |
| JP | 09-288237 | 11/1997 |
| JP | 10-333053 | 12/1998 |
| JP | 2002-202459 | 7/2002 |
| JP | 2003-222801 | 8/2003 |
| WO | 03/100086 | 12/2003 |
| WO | 2005101086 A2 | 10/2005 |

OTHER PUBLICATIONS

European Search Report dated Dec. 23, 2010, corresponding to European Appln. No. 10167933.0.

Office Action issued in connection with Japanese Patent Application No. 2009-163775, dated Mar. 5, 2013. (4 pages).

* cited by examiner

F I G . 5
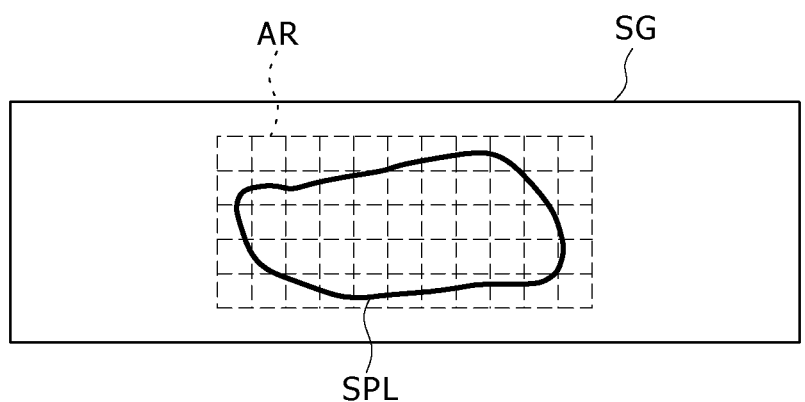

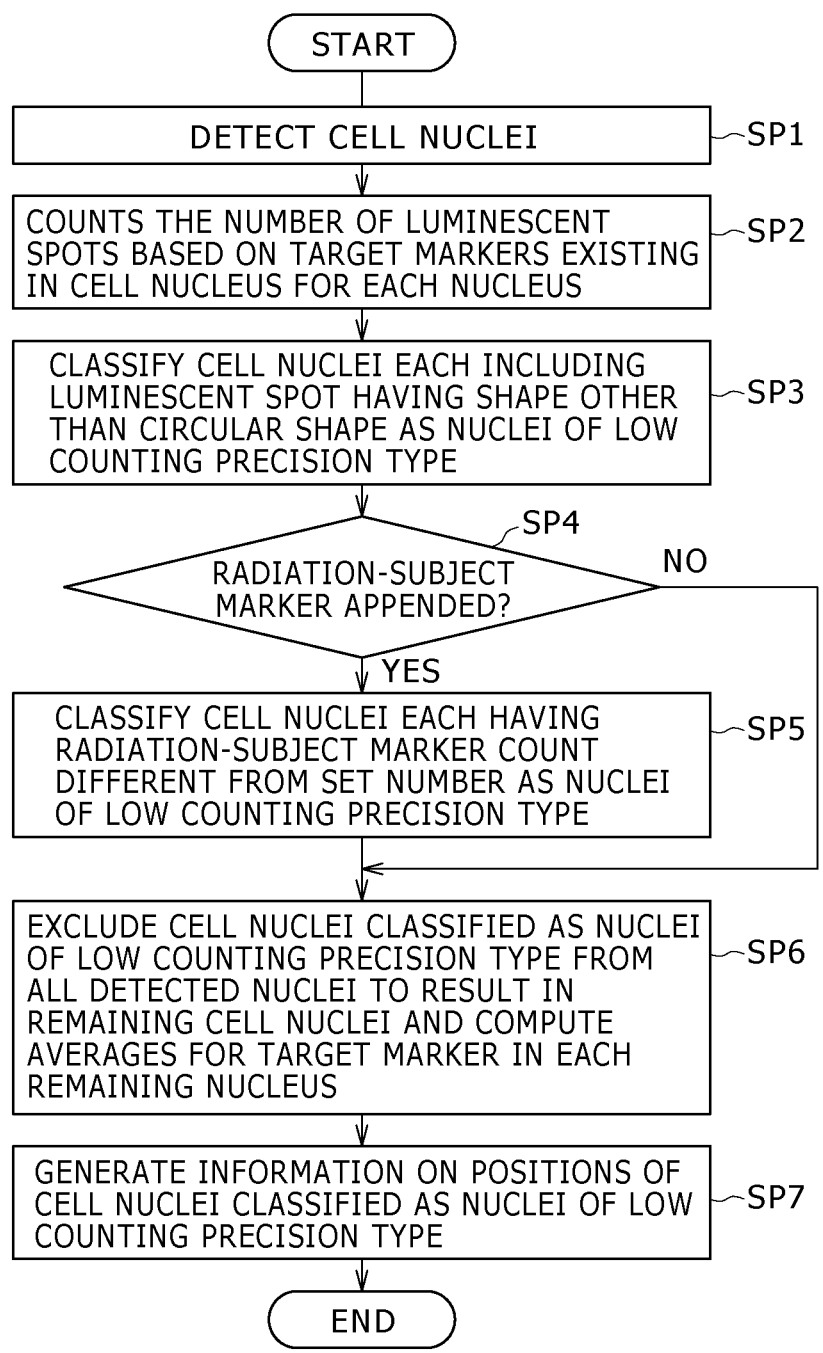

FIG.7A
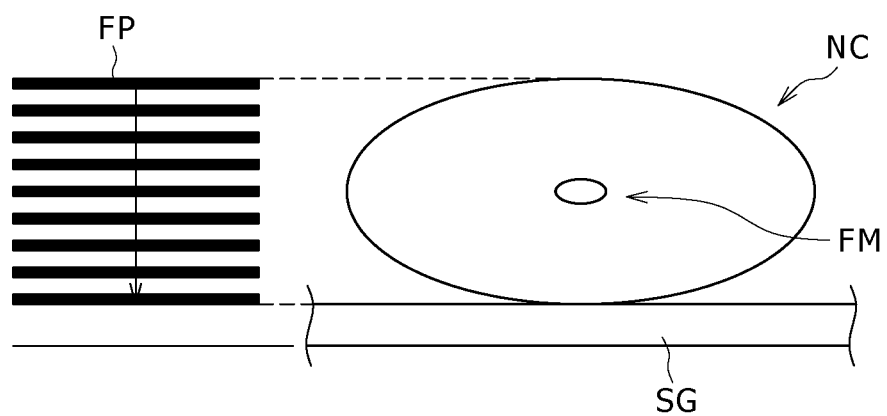
FIG.7B
FIG.7C
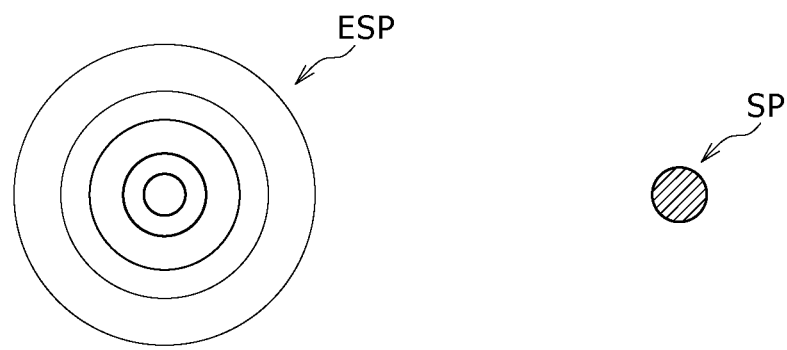

FLUORESCENT-IMAGE ACQUISITION APPARATUS, FLUORESCENT-IMAGE ACQUISITION METHOD AND FLUORESCENT-IMAGE ACQUISITION PROGRAM

CROSS REFERENCES TO RELATED APPLICATIONS

The present application claims priority to Japanese Priority Patent Application JP 2009-163775 filed in the Japan Patent Office on Jul. 10, 2009, the entire content of which is hereby incorporated by reference.

BACKGROUND

In general, the present application relates to a fluorescent-image acquisition apparatus, a fluorescent-image acquisition method adopted by the fluorescent-image acquisition apparatus and a fluorescent-image acquisition program implementing the fluorescent-image acquisition method. For example, the present application can be well applied to a field in which a fluorescently-stained tissue segment is observed.

A tissue segment firmly held on a slide glass plate is a typical biological sample. If necessary, the tissue segment is stained before being kept somewhere. In general, when the tissue-segment keeping period becomes long, the tissue segment deteriorates and/or the color of the tissue segment fades away. Usually, a microscope is used for observing a tissue segment serving as a biological sample. If the tissue segment has deteriorated and/or the color of the tissue segment has faded away, however, visibility provided by the microscope as the visibility of the tissue segment becomes bad. In addition, in some cases, such a biological sample is diagnosed at a facility outside a hospital at which the sample has been produced. In such cases, the biological sample is generally sent from the hospital to the facility by mail. That is to say, it takes time to send the biological sample from the hospital to the facility.

In order to solve the problem described above, there has been proposed an apparatus for keeping a biological sample as image data. For further information on such an apparatus, the reader is suggested to refer to documents such as Japanese Patent Laid-open No. 2003-222801.

SUMMARY

By the way, in an operation to take a fluorescent image of a fluorescently-stained tissue segment, the focal point is moved from position to position at intervals determined in advance in the thickness direction of the fluorescently-stained tissue segment. Then, a fluorescent image taken at every focal point is used for generating image data. In this way, it is possible to acquire fluorescent images without dropping a fluorescent marker which indicates molecules as the subject of the operation to take an image. In this case, however, the number of fluorescent images for one biological sample increases considerably. As a result, the processing load per biological sample and the amount of image data per biological sample also rise inevitably.

If the interval between the positions of the moving focal point is increased in the thickness direction of the biological sample, on the other hand, the number of fluorescent images for one biological sample can be reduced. As a result, the processing load per biological sample and the amount of image data per biological sample can also be decreased as well. With the interval between the positions of the moving focal point increased in the thickness direction of the biological sample, however, if an objective lens with a small focal-point depth is used in an operation to take a fluorescent image, it is quite within the bounds of possibility that a fluorescent marker indicating molecules as the subject of the operation to take the image is dropped. As a result, the precision of an operation to measure fluorescent markers deteriorates.

Addressing the problems described above, inventors have innovated a fluorescent-image acquisition apparatus capable of sustaining the precision of an operation to measure fluorescent markers at a certain level while reducing the processing load and the amount of image data, innovated a fluorescent-image acquisition method to be adopted by the fluorescent-image acquisition apparatus and innovated a fluorescent-image acquisition program implementing the fluorescent-image acquisition method.

In order to solve the problems described above, the embodiments provide a fluorescent-image acquisition apparatus which employs:

an excitement-light source for radiating excitement light to a fluorescent marker on a biological sample;

a dark-field radiation system;

an objective lens for enlarging an image of a member of the biological sample;

an image pickup device for forming the member image enlarged by the objective lens to appear as a fluorescent image of the member;

a focal-point movement control section configured to move the focal point of the objective lens in the thickness direction of the biological sample; and an image-pickup control section configured to expose the image pickup device to light and acquire the member image enlarged by the objective lens to appear as the fluorescent image of the member from the image pickup device while the focal point of the objective lens is being moved in the thickness direction of the biological sample.

In addition, the embodiments also provide a fluorescent-image acquisition method which includes:

a light radiation step of carrying out dark-field radiation on a biological sample having a fluorescent marker appended to the biological sample;

a focal-point movement step of moving the focal point of an objective lens in the thickness direction of the biological sample having the fluorescent marker appended to the biological sample;

an exposure step of exposing an image pickup device, on which an image enlarged by the objective lens to appear as a fluorescent image of a member of the biological sample is created, to light while the focal point of the objective lens is being moved in the thickness direction of the biological sample at the focal-point movement step; and an image acquisition step of acquiring the image enlarged by the objective lens to appear as the fluorescent image of the member of the biological sample from the image pickup device when triggered at the end point of the movement made by the focal point of the objective lens at the focal-point movement step.

On top of that, the embodiments also provide a fluorescent-image acquisition program to be executed by a computer to carry out processing which includes:

a light radiation process of carrying out dark-field radiation on a biological sample having a fluorescent marker appended to the biological sample;

a focal-point movement process of moving the focal point of an objective lens in the thickness direction of the biological sample having the fluorescent marker appended to the biological sample;

an exposure process of exposing an image pickup device, on which an image enlarged by the objective lens to appear as a fluorescent image of a member of the biological sample is created, to light while the focal point of the objective lens is being moved in the thickness direction of the biological sample at the focal-point movement process; and an image acquisition process of acquiring the image enlarged by the objective lens to appear as the fluorescent image of the member of the biological sample from the image pickup device when triggered at the end point of the movement in the thickness direction of the biological sample made by the focal point of the objective lens.

As described above, in accordance with the embodiments, a period in which the focal point of the objective lens is being moved in the thickness direction is taken as the exposure period and a fluorescent image is acquired at the end of the exposure period. Thus, the number of times to acquire fluorescent images is small in comparison with a configuration in which the focal point of an objective lens is moved from position to position at intervals determined in advance in the thickness direction of the biological sample. As a result, it is possible to reduce the processing load per biological sample and the amount of image data per biological sample.

In addition, since a period in which the focal point of the objective lens is being moved in the thickness direction of the biological sample is taken as the exposure period, even if a fluorescent marker exists at any one of positions arranged in the thickness direction of the biological sample, the fluorescent marker is perceived as an equivalent luminescent spot. Thus, without regard to the depth of the focal point of the objective lens in use, it is possible to prevent the fluorescent marker from being dropped.

In this way, it is possible to realize a fluorescent-image acquisition apparatus capable of sustaining the precision of an operation to measure fluorescent markers at a certain level while reducing the amount of image data, realize a fluorescent-image acquisition method to be adopted by the fluorescent-image acquisition apparatus and realize a fluorescent-image acquisition program implementing the fluorescent-image acquisition method.

Additional features and advantages are described herein, and will be apparent from the following Detailed Description and the figures.

BRIEF DESCRIPTION OF THE FIGURES

FIG. 5 is a rough explanatory diagram to be referred to in description of a process of acquiring an image for each area of a biological sample;

FIG. 6 shows a flowchart representing the procedure of processing to count the number of genes;

FIGS. 7A to 7C are a plurality of diagrams roughly showing a relation between the movement of the focal point of an objective lens employed in the biological-sample image acquisition apparatus in the thickness direction of a biological sample and a luminescent spot based on a fluorescent marker on the sample;

DETAILED DESCRIPTION

Figure 1:
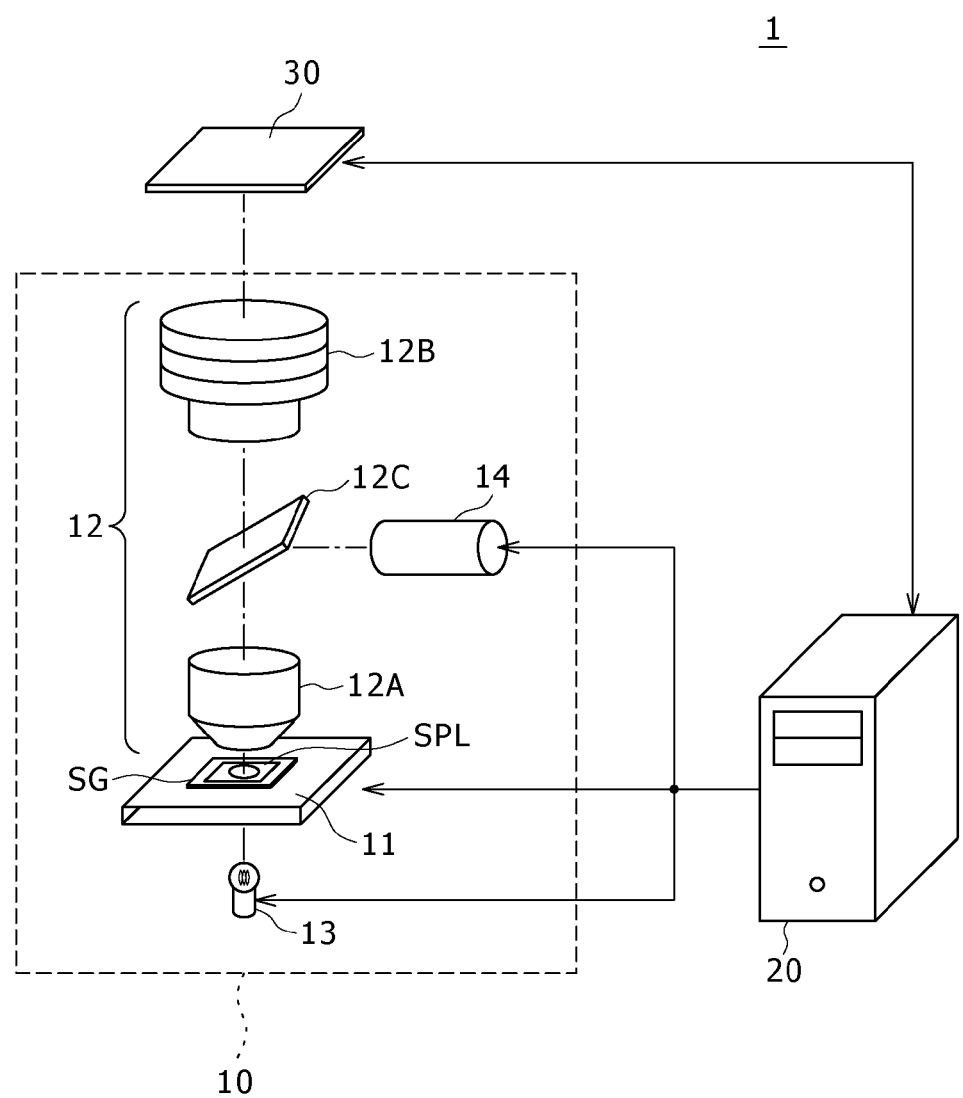
FIG. 1 is a diagram roughly showing the configuration of a biological-sample image acquisition apparatus according to an embodiment.

The present application will be described in detail below with reference to the drawings according to an embodiment.
1: Embodiment
1-1: Configuration of the Biological-Sample Image Acquisition Apparatus
1-2: Configuration of the Data Processing Section
1-3: Concrete Processes of the Sample-Image Acquisition Processing
1-4: Effects and Others
2: Other Embodiments 1: Embodiment 1-1: Configuration of the Biological-Sample Image Acquisition Apparatus FIG. 1 is a diagram roughly showing the configuration of a biological-sample image acquisition apparatus 1 according to an embodiment. As shown in the figure, the biological-sample image acquisition apparatus 1 is configured to employ a microscope 10, a data processing section 20 and an image pickup device 30. The microscope 10 employs a movable stage 11, objective lenses 12, a radiation system 13 and an excitement-light source 14.

The movable stage 11 employed in the microscope 10 has a surface on which a biological sample SPL can be placed. In addition, the movable stage 11 can be moved in directions parallel to the surface and a direction perpendicular to the surface. That is to say, the movable stage 11 can be moved in directions parallel to the x-y surface and parallel to the z-axis direction.

The biological sample SPL is provided by firmly holding a tissue segment or a stained cell on a slide glass plate SG provided on the surface of the movable stage 11 by adoption of a sample fixing method determined in advance. The tissue segment is made from typically a junction tissue such as a drop of blood, an epithelium tissue or both the junction tissue and the epithelium tissue. If necessary, a dyeing color is applied to the tissue segment or the stained cell. The dyeing color is by no means limited to the ordinary dyeing colors which are represented by the HE (Hematoxylin Eosin) dyeing color, the giemsa dyeing color and the Papanicolaou dying color, but the dyeing color can also be a fluorescent dyeing color which is prepared by adoption of the FISH (Fluorescence In-Situ Hybridization) technique or the enzyme antibody technique.

In the microscope 10, on a specific side of the movable stage 11, the objective lenses 12 are provided. On a side opposite to the specific side in the microscope 10, on the other hand, the radiation system 13 is provided. The radiation system 13 is capable of switching the light radiation from a bright-field radiation process to a dark-field radiation process and vice versa.

In a bright-field speculum mode, light emitted from the radiation system 13 in a bright-field radiation process propagates through a hole provided on the movable stage 11 and arrives at the biological sample SPL which is provided on the surface of the movable stage 11 on the specific side of the movable stage 11.

The objective lenses 12 include a first objective lens 12A and a second objective lens 12B. Reflection and scattering of light radiated by the radiation system 13 result in an image of a member of the biological sample SPL. In the objective lenses 12 employed in the microscope 10, the first objective lens 12A and the second objective lens 12B enlarge the image of the member of the biological sample SPL at a predetermined magnifying power. The image enlarged by the first objective lens 12A and the second objective lens 12B is projected on the imaging surface of the image pickup device 30.

In a dark-field speculum mode, on the other hand, light emitted from the radiation system 13 in a dark-field radiation process propagates through the hole provided on the movable stage 11 and arrives at the biological sample SPL which is provided on the surface of the movable stage 11 on the specific side of the movable stage 11 as described above. However, the light arriving at the biological sample SPL in the dark-field speculum mode is radiated light cutting out background light of the biological sample SPL.

In addition, in the dark-field speculum mode, the excitement-light source 14 employed in the microscope 10 radiates excitement light to a fluorescent marker used for expressing a fluorescent dyeing color of the biological sample SPL. In the following description, the excitement light radiated by the excitement-light source 14 to a fluorescent marker is referred to simply as excitement light. The objective lenses 12 also include a dichroic mirror 12C which is provided between the first objective lens 12A and the second objective lens 12B. In the microscope 10, the excitement light propagates to the first objective lens 12A after being reflected by the dichroic mirror 12C. The first objective lens 12A focuses the excitement light on the biological sample SPL provided on the surface of the movable stage 11.

With a fluorescent color applied to the biological sample SPL as a color expressed by a fluorescent marker, the fluorescent marker appended to a target member of the biological sample SPL emits light due to the excitement light focused thereon. In the following description, the light emitted by the target member of the biological sample SPL is referred to as marker light. The marker light emitted by the target member of the biological sample SPL arrives at the first objective lens 12A.

In the microscope 10, an image obtained from the marker light as an image of the target member of the biological sample SPL is enlarged at a predetermined magnifying power determined by the first objective lens 12A and the second objective lens 12B. Then, the microscope 10 projects the member image enlarged by the first objective lens 12A and the second objective lens 12B on the imaging surface of the image pickup device 30.

Figure 2A:
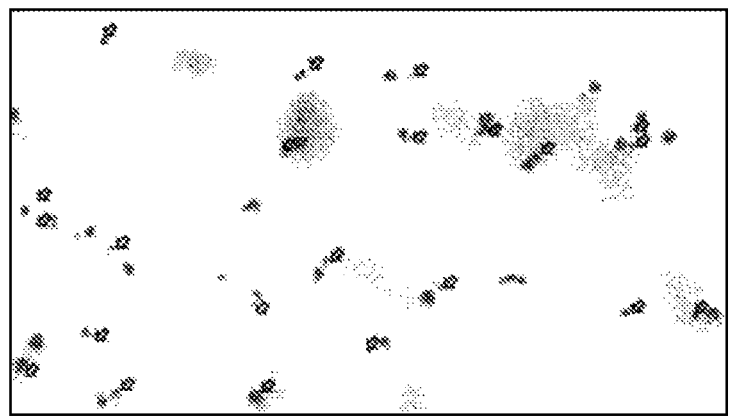
FIGS. 2A and 2B are a plurality of diagrams showing a fluorescent image.
Figure 2B:
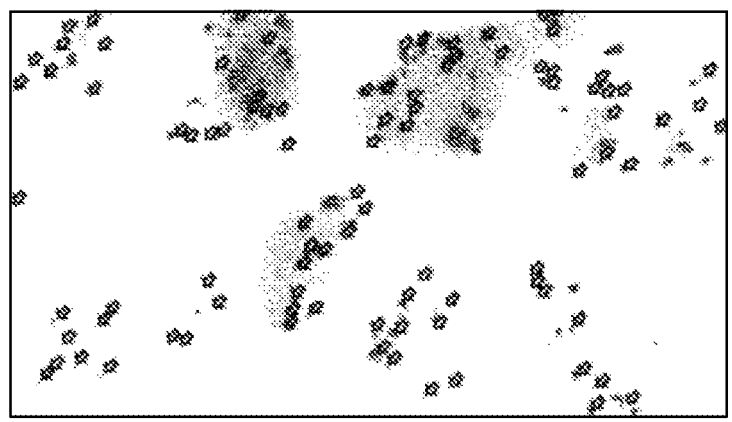

FIGS. 2A and 2B are a plurality of diagrams each showing a fluorescent image of a biological sample SPL. To be more specific, FIG. 2A is a diagram showing a typical fluorescent image of a lacteal gland (or milk gland) tissue taken from a normal person whereas FIG. 2B is a diagram showing another typical fluorescent image of a lacteal gland (or milk gland) tissue of a patient of the breast cancer. The fluorescent image shown in each of the diagrams of FIGS. 2A and 2B is obtained by carrying out a hybridization process according to the FISH technique on HER2 (Human Epithelial growth factor Receptor type 2) genes in the lacteal gland (or milk gland) tissue and on a probe (PathVysion of a HER2 DNA probe kit which is made by Abbott).

As shown in the diagrams of FIGS. 2A and 2B, in comparison with the normal lacteal gland (or milk gland) tissue, the malignant lacteal gland (or milk gland) tissue has many fluorescent markers which are each a labeling substance pointed to by an arrow. As also obvious from the diagrams of FIGS. 2A and 2B, the HER2 genes grow proliferously in a malignant tumor such as the breast cancer, the ovary cancer, the uterus cancer, the stomach cancer, the bladder cancer, the small cell lung cancer or the prostate cancer. Thus, the HER2 genes can be visually perceived as the fluorescent markers indicating the progression of the malignant tumor. In the bright-field speculum mode, the radiation system 13 is driven to carry out a bright-field radiation process in order to form an image of a member of the biological sample SPL put in a bright-field state on the imaging surface of the image pickup device 30. Then, the data processing section 20 acquires the image from the image pickup device 30 and stores the image as data having a format determined in advance. In the following description, the stored data having a format determined in advance is referred to as sample data.

In the dark-field speculum mode, on the other hand, the radiation system 13 is driven to carry out a dark-field radiation process and the excitement-light source 14 is driven to radiate excitement light to the biological sample SPL. Then, an image of the biological sample SPL put in a dark-field state is formed on the imaging surface of the image pickup device 30. Finally, the data processing section 20 acquires the image from the image pickup device 30 and stores the image as sample data.

In this way, the biological-sample image acquisition apparatus 1 is capable of saving bright-field and dark-field images of the biological sample SPL placed on the slide glass plate SG as sample data. Thus, in comparison with a configuration in which the slide glass plate SG itself is saved, the biological-sample image acquisition apparatus 1 is capable of keeping information on the biological sample SPL for a long time without deteriorating the fixing state of the biological sample SPL on the slide glass plate SG, the dyeing color state of the biological sample SPL and other states.

1-2: Configuration of the Data Processing Section

Figure 3:
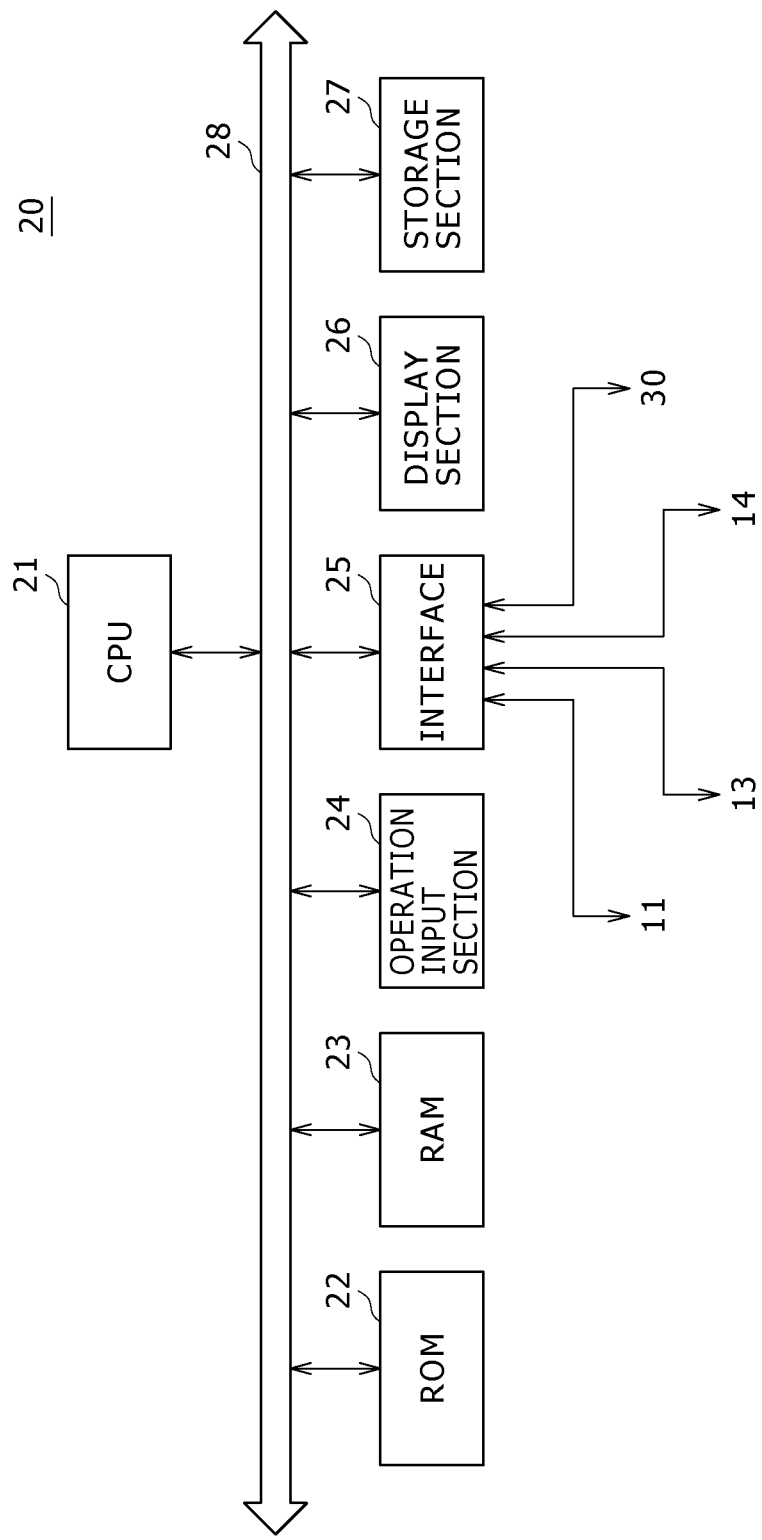
FIG. 3 is a block diagram showing the configuration of a data processing section.

FIG. 3 is a block diagram showing the configuration of the aforementioned data processing section 20 employed in the biological-sample image acquisition apparatus 1. The data processing section 20 is explained by referring to this figure as follows. As shown in this figure, the data processing section 20 employs a CPU (Central Processing Unit) 21, a ROM (Read Only Memory) 22, a RAM (Random Access Memory) 23, an operation input section 24, an interface 25, a display section 26, a storage section 27 and a bus 28. The CPU 21 serving as a section for carrying out various kinds of control is connected to various kinds of hardware.

To put it more concretely, the CPU 21 is connected by the bus 28 to the ROM 22, the RAM 23, the operation input section 24, the interface 25, the display section 26 and the storage section 27. The RAM 23 is the work memory of the CPU 21. The operation input section 24 is a section to be carried out by the user to enter a variety of commands to the data processing section 20.

The CPU 21 is a section for executing the programs stored in the ROM 22 in order to carry out various kinds of processing. The interface 25 is a section serving as an interface with external sections such as the movable stage 11, the radiation system 13, the excitement-light source 14 and the image pickup device 30 which are shown in the diagram of FIG. 1

The display section 26 is typically a liquid-crystal display section, an EL (Electro Luminescence) display section or a plasma display section. The storage section 27 is typically a magnetic disc, a semiconductor memory or an optical disc. A representative example of the magnetic disc is an HD (hard disc). The storage section 27 can also be a portable memory such as a USB (Universal Serial Bus) memory or a CF (Compact Flash) memory.

The CPU 21 selects a specific program among the programs stored in the ROM 22 in accordance with a command received from the operation input section 24 and loads the specific program into the RAM 23. Then, the CPU 21 executes the specific program loaded in the RAM 23 in order to properly control the display section 26 and the storage section 27.

In addition, the CPU 21 executes the specific program loaded in the RAM 23 in order to properly control the movable stage 11, the radiation system 13, the excitement-light source 14 and the image pickup device 30 through the interface 25.

1-3: Concrete Processes of the Sample-Image Acquisition Processing

When an image acquisition command is received from the operation input section 24, the CPU 21 loads a program associated with the command from the ROM 22 to the RAM 23. The image acquisition command is a command requesting the data processing section 20 employed in the biological-sample image acquisition apparatus 1 to acquire an image of the biological sample SPL, to which the fluorescent dyeing process has been applied, from the image pickup device 30. In the following description, an image of the biological sample SPL to which the fluorescent dyeing process has been applied is referred to as a sample fluorescent image.

Figure 4:
FIG. 4 is a block diagram showing the functional configuration of a CPU as a configuration prevailing in an operation to acquire an image of a biological sample.

Then, the CPU 21 executes the program associated with the image acquisition command in order to function as a light-source control section 41, a stage-movement control section 42, a fluorescent-image acquisition section 43, a gene counting section 44 and a data recording section 45 as shown in a block diagram of FIG. 4. FIG. 4 is a block diagram showing the functional configuration of the CPU 21 as a configuration prevailing in the operation to acquire a sample fluorescent image of the biological sample SPL.

The light-source control section 41 is a functional section for driving the radiation system 13 to carry out a dark-field radiation process and driving the excitement-light source 14 to radiate excitement light.

The stage-movement control section 42 is a functional section for sequentially moving the movable stage 11 in order to position sample members of the biological sample SPL at a location in an image acquisition range AR. A sample member is a member, a sample fluorescent image of which is to be acquired. FIG. 5 is a rough explanatory diagram to be referred to in description of a process to acquire an image for each area of a biological sample SPL. The stage-movement control section 42 assigns the biological sample SPL to the image acquisition range AR as shown in the explanatory diagram of FIG. 5. In FIG. 5, areas of the biological sample SPL to be assigned to the image acquisition range AR do not overlap each other. It is to be noted, however, that areas of the biological sample SPL to be assigned to the image acquisition range AR may overlap each other.

In every operation to position the sample members serving as the subject of the image acquisition process at a location in an image acquisition range AR, the stage-movement control section 42 moves the movable stage 11 in the Z-axis direction in order to shift the focal point of the first objective lens 12A for the sample members in the direction of the thickness of the biological sample SPL. The Z-axis direction is the optical direction of the first objective lens 12A.

In every operation carried out by the stage-movement control section 42 to position the sample members serving as the subject of the image acquisition process at a location in an image acquisition range AR, the fluorescent-image acquisition section 43 exposes the image pickup device 30 to light during an exposure period which is started at a point of time the movement of the movable stage 11 in the Z-axis direction (that is, the optical direction of the first objective lens 12A) is commenced and terminated at a point of time the movement of the movable stage 11 in the Z-axis direction is ended.

At the point of time the movement of the movable stage 11 in the Z-axis direction (that is, the optical direction of the first objective lens 12A) is ended, the fluorescent-image acquisition section 43 acquires fluorescent images of the sample members. The acquired fluorescent images of the sample members are images generated during the exposure period which is started at the point of time the movement of the movable stage 11 in the Z-axis direction is commenced and terminated at the point of time the movement of the movable stage 11 in the Z-axis direction is ended.

The fluorescent-image acquisition section 43 is a functional section for generating a sample fluorescent image by joining the acquired fluorescent images of the sample members, which are assigned to the image acquisition range AR, by adoption of a joining algorithm determined in advance. The sample fluorescent image is the fluorescent image of the entire biological sample SPL. The sample fluorescent image is enlarged at a magnifying power which is determined by the first objective lens 12A and the second objective lens 12B.

After the fluorescent-image acquisition section 43 has generated a sample fluorescent image, on the basis of information set to serve as information desired for a counting operation, the gene counting section 44 counts the number of fluorescent markers each labeling a gene serving as a target for every cell nucleus. In the following description, the gene serving as a target is referred to as a target gene whereas a fluorescent marker labeling a target gene is referred to as a target marker.

The information set to serve as information for a counting operation includes a color expressed by a target marker and a color expressed by a fluorescent marker labeling a cell nucleus. In the following description, a fluorescent marker labeling a cell nucleus is referred to as a nucleus marker, a color expressed by a target marker is referred to as a target-marker color whereas a color expressed by the nucleus marker is referred to as a nucleus-marker color.

If a fluorescent marker labeling a gene to which light is to be radiated is used, the number of such genes existing in a normal cell is set. In this case, a color expressed by the fluorescent marker labeling a gene is also set. In the following description, a fluorescent marker labeling a gene to which light is to be radiated is referred to as a radiation-subject marker and a color expressed by a radiation-subject marker is referred to as a radiation-subject marker color.

The information set to serve as information for a counting operation is determined uniquely by the manufacturer of a probe used in a process of applying a fluorescent dyeing color and by usage conditions such as the type of the fluorescent marker. To put it more concretely, in the case of the HER2 DNA probe kit made by Abbott to be used as a probe kit for producing the fluorescent images shown in the diagrams of FIGS. 2A and 2B, the target-marker color of the HER2 gene is set at the red color whereas the nucleus-marker color thereof is set at the blue color. In this case, a gene placed at a location adjacent to the HER2 gene on the dyeing-colored body is used as a radiation-subject gene and the radiation-subject marker color of this radiation-subject gene is set at the yellow-green color. Moreover, the number of such genes is set at 2.

In addition, as a method for setting the information for a counting operation, it is possible to adopt a technique whereby the user is requested to enter a usage condition. Then, from this usage condition and a database associating the radiation-subject marker color with the number of radiation-subject genes, the marker color and the number of radiation-subject genes are found.

By the way, the usage condition is entered by adoption of a usage-condition entering technique described as follows. For example, the user may enter a usage condition by operating typically a keyboard in order to specify a number representing the manufacturer of the probe or a number representing the type of the fluorescent marker. As an alternative technique, the manufacturer of the probe or the type of the fluorescent marker is pulled down to be displayed on a screen and, then, the user operates a keyboard in order to select a desired manufacturer of the probe or a desired type of the fluorescent marker from the display appearing on the screen. In addition, the database cited earlier can be obtained from a network such as the Internet and stored in the storage section 27. Then, if necessary, the database is updated from time to time.

FIG. 6 shows a flowchart representing the procedure of processing to count the number of genes. The procedure of processing carried out by the gene counting section 44 to count the number of genes is explained by referring to the flowchart shown in FIG. 6.

If the fluorescent-image acquisition section 43 has generated a sample fluorescent image, the gene counting section 44 starts the procedure of the processing to count the number of genes by carrying out a first step SP1 of the flowchart representing the procedure. At the first step SP1, the gene counting section 44 detects cell nuclei and then continues the procedure of the processing to count the number of genes to a second step SP2. The detected cell nucleus is an area of pixels which each have the nucleus marker color set as a color expressed by the cell nucleus and each have a luminance not smaller than a threshold value determined in advance.

At the second step SP2, for every cell nucleus detected at the first step SP1, the gene counting section 44 counts the number of luminescent spots each based on one of target markers existing in the cell nucleus. Then, the flow of the processing procedure goes on to a third step SP3.

In the dark-field speculum mode, a structure having dimensions smaller than about several tens of nanometers is generally taken as a luminescent spot mentioned above. Thus, a target marker or a radiation-subject marker is used as a luminescent spot in an image-taking operation. In this embodiment, the image pickup device 30 is exposed to light during an exposure period which is started at the point of time the movement of the movable stage 11 in the Z-axis direction (that is, the optical direction of the first objective lens 12A) is commenced and terminated at the point of time the movement of the movable stage 11 in the Z-axis direction is ended. Thus, the exposure of the image pickup device 30 to light results in a defocused luminescent spot which is referred to hereafter as an expanded luminescent spot.

Details are described as follows. FIGS. 7A to 7C are a plurality of diagrams roughly showing a relation between the movement of the focal point of the first objective lens 12A in the thickness direction of the biological sample SPL and the luminescent spot based on a fluorescent marker FM on the sample SPL. To be more specific, FIG. 7A is a diagram showing a changing state of matching of the focal-point plane FP of the first objective lens 12A and a fluorescent marker FM. To put it more concretely, the matching state shown in the diagram of FIG. 7A gradually changes from a state in which the focal-point plane FP of the first objective lens 12A does not match the fluorescent marker FM to a state in which the focal-point plane FP matches the fluorescent marker FM and, finally, to a state in which the focal-point plane FP again does not match the fluorescent marker FM. On the other hand, FIG. 7B is a diagram showing an expanded luminescent spot ESP whereas FIG. 7C is a diagram showing a luminescent spot SP taken in an image taking operation carried out in a state in which the focal-point plane FP of the first objective lens 12A matches the fluorescent marker FM. As a result of the changing state described above, the image of the expanded luminescent spot ESP is larger than the image of the luminescent spot SP as is obvious from the diagrams of FIGS. 7B and 7C.

Nevertheless, the shape of the expanded luminescent spot ESP itself does not change from a circular shape. However, the shape of the spot SP is not circular anymore in the case of two or more fluorescent markers FM placed at locations adjacent to each other or in the case of portions of two or more fluorescent markers FM overlapping each other with the biological sample SPL viewed in the thickness direction.

Figure 8A:
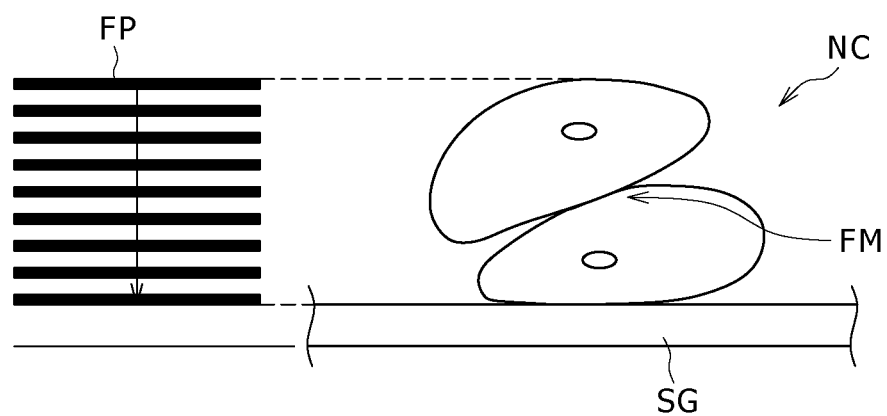
FIGS. 8A to 8C are a plurality of diagrams roughly showing a relation between the movement of the focal point of the objective lens in the thickness direction of a biological sample and luminescent spots each based on a fluorescent marker on the sample for a case in which portions of the fluorescent markers overlap each other in the thickness direction.
Figure 8B:
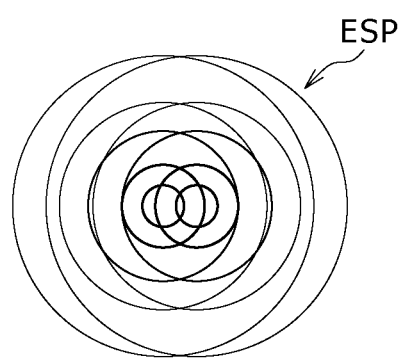
Figure 8C:
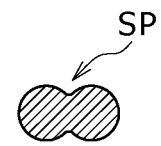

For the purpose of comparison with the diagrams of FIGS. 7A to 7C, FIGS. 8A to 8C are given as a plurality of diagrams roughly showing a relation between the movement of the focal point of the first objective lens 12A in the thickness direction of the biological sample SPL and luminescent spots each based on a fluorescent marker FM on the sample SPL for a case in which portions of the fluorescent markers FM overlap each other in the thickness direction. To be more specific, FIG. 8A is a diagram showing a changing state of matching of the focal-point plane FP of the first objective lens 12A and the fluorescent markers FM whereas FIG. 8B is a diagram showing an expanded luminescent spot ESP. FIG. 8C is a diagram showing a luminescent spot SP taken in an image taking operation carried out in a state in which the focal-point plane FP of the first objective lens 12A matches the fluorescent markers FM. As is obvious from the diagrams of FIGS. 8A to 8C, it becomes difficult to determine the number of target markers serving as the base of a luminescent spot SP in the case of two or more fluorescent markers FM placed at locations adjacent to each other or in the case of portions of two or more fluorescent markers FM overlapping each other with the biological sample SPL viewed in the thickness direction.

For the reasons described above, the process of the second step SP2 is carried out to count particular luminescent spots each based on a target markers. A particular luminescent spot is a luminescent spot that expresses the set target-marker color and satisfies a condition requiring that the shape of the luminescent spot SP be circular. It is to be noted that the condition requiring that the shape of the luminescent spot SP be circular may imply a case in which an area including adjacent pixels each having a luminance not smaller than a threshold value determined in advance is treated as a luminescent spot SP and the ratio of the major axis of the area to the minor axis of the area is not smaller than a threshold ratio determined in advance.

At the third step SP3, the gene counting section 44 selects particular cell nuclei from cell nuclei detected at the first step SP1 in order to classify the selected particular cell nuclei as a special class of cell nuclei. A particular cell nucleus is defined as a cell nucleus in which there is a luminescent spot based on a target marker to appear as a luminescent spot not satisfying the condition requiring that the shape of the luminescent spot SP be circular. A particular cell nucleus is a cell nucleus for which the precision of the operation to count the number of luminescent spots each based on a target marker per cell nucleus is low. In the following description, the type of a particular cell nucleus is referred to as a low counting precision cell-nucleus type. Then, the flow of the processing procedure goes on to a fourth step SP4.

At the fourth step SP4, the gene counting section 44 determines whether or not the number of radiation-subject genes and a radiation-subject marker color have been set. If the gene counting section 44 determines that the number of radiation-subject genes and a radiation-subject marker color have been set, the flow of the processing procedure goes on to a fifth step SP5. If the gene counting section 44 determines that the number of radiation-subject genes and/or a radiation-subject marker color have not been set, on the other hand, the flow of the processing procedure goes on to a sixth step SP6. As described earlier, a radiation-subject gene is a gene which serves as a subject of light radiation.

At the fifth step SP5, the gene counting section 44 counts the number of luminescent spots each based on a radiation-subject marker in a cell nucleus for each of the cell nuclei detected at the first step SP1.

By the way, much like the second step SP2, the process of the second step SP5 is carried out to count particular luminescent spots each based on a radiation-subject marker. A particular luminescent spot is a luminescent spot that expresses the set radiation-subject marker color and satisfies a condition requiring that the shape of the luminescent spot SP be circular. It is to be noted that the condition requiring that the shape of the luminescent spot SP be circular for the radiation-subject marker can be the same condition as that for the target marker or a condition different from that for the target marker. As described before, a radiation-subject marker is a marker that serves as a subject of light radiation.

Figure 9A:
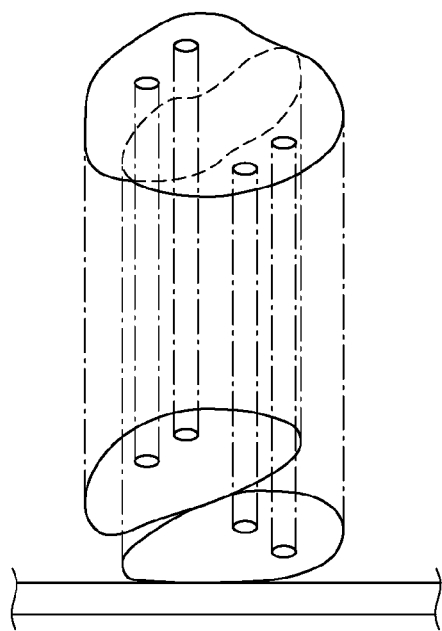
FIGS. 9A and 9B are a plurality of diagrams showing a sample fluorescent image in which the number of markers each serving as the subject of light radiation is different from a prescribed number.
Figure 9B:
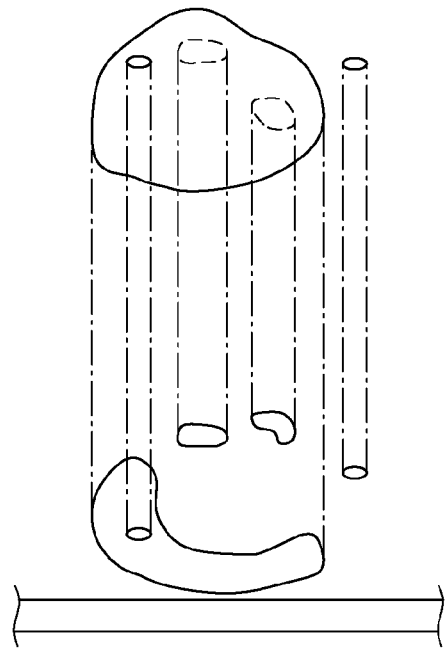

FIGS. 9A and 9B are a plurality of diagrams each showing a sample fluorescent image in which the number of markers each serving as the subject of light radiation is different from a prescribed number representing the number of genes each serving as the subject of light radiation. To be more specific, FIG. 9A is a diagram showing a sample fluorescent image in which the number of markers each serving as the subject of light radiation is greater than the number of genes each serving as the subject of light radiation whereas FIG. 9B is a diagram showing a sample fluorescent image in which the number of markers each serving as the subject of light radiation is smaller than the number of genes each serving as the subject of light radiation.

As shown in the diagram of FIG. 9A, in the case of a cell nucleus for which the number of markers each serving as the subject of light radiation is greater than the number of genes each serving as the subject of light radiation, it is quite within the bounds of possibility that the number of markers each serving as the subject of light radiation is greater than the number of genes each serving as the subject of light radiation because a plurality of call nuclei overlap each other in the thickness direction of the biological sample SPL. With a plurality of cell nuclei overlapping each other in the thickness direction of the biological sample SPL, the number of luminescent spots each based on a target marker in the cell nuclei is not a result of a counting operation carried out by correctly assuming that the target markers exist in one cell nucleus.

As shown in the diagram of FIG. 9B, in the case of a cell nucleus for which the number of markers each serving as the subject of light radiation is smaller than the number of genes each serving as the subject of light radiation, on the other hand, it is quite within the bounds of possibility that the number of markers each serving as the subject of light radiation is smaller than the number of genes each serving as the subject of light radiation because some cell nuclei have been damaged as a result of cancer progression or as a result of a surgery. Also in this case, the number of luminescent spots each based on a target marker in the cell nuclei is not a result of a counting operation carried out by correctly assuming that the target markers exist in one cell nucleus.

It is to be noted that FIGS. 9A and 9B show sample fluorescent images for the HER2 DNA probe kit which is made by Abbott to serve as a probe kit producing the sample fluorescent images shown in the diagrams of FIGS. 2A and 2B. That is to say, in the case of a normal cell nucleus, the number of genes each serving as the subject of light radiation in a cell nucleus is two as shown in the diagram of FIG. 9A.

For the reason described above, at the fifth step SP5, the gene counting section 44 selects particular cell nuclei from cell nuclei detected at the first step SP1 in order to classify the selected particular cell nuclei as a special class of cell nuclei. A particular cell nucleus is a cell nucleus in which the number of markers each serving as the subject of light radiation is different from the number of genes each serving as the subject of light radiation as is the cases shown in the diagrams of FIGS. 9A and 9B. A particular cell nucleus is a cell nucleus for which the precision of the operation to count the number of luminescent spots each based on a marker per cell nucleus is low. In the following description, the type of a particular cell nucleus is referred to as a low counting precision cell-nucleus type. Then, the flow of the processing procedure goes on to the sixth step SP6.

At the sixth step SP6, the gene counting section 44 excludes low counting precision cell nuclei from cell nuclei detected at the first step SP1 to result in remaining cell nuclei. Then, the gene counting section 44 computes an average of target-marker counts each obtained for one of the remaining cell nuclei as an average per cell nucleus. If the gene counting section 44 has determined at the fourth step SP4 that the number of radiation-subject genes and/or a radiation-subject marker color have not been set, the low counting precision cell nuclei excluded from the cell nuclei detected at the first step SP1 are the low counting precision cell nuclei determined at the third step SP3.

If the gene counting section 44 has determined at the fourth step SP4 that the number of radiation-subject genes and a radiation-subject marker color have been set, on the other hand, the low counting precision cell nuclei excluded from the cell nuclei detected at the first step SP1 are the low counting precision cell nuclei determined at the third step SP3, the low counting precision cell nuclei determined at the fifth step SP5 or both the low counting precision cell nuclei determined at the third step SP3 and the low counting precision cell nuclei determined at the fifth step SP5. In this case, the gene counting section 44 computes an average of target-marker counts each obtained for one of the remaining cell nuclei as an average per cell nucleus, an average of radiation-subject-marker counts each obtained for one of the remaining cell nuclei as an average per cell nucleus and an average of quotients each obtained by dividing the number of luminescent spots each based on a target marker for any particular one of remaining cell nuclei by the number of luminescent spots each based on a radiation-subject marker for the same particular remaining cell nucleus. Then, the flow of the processing procedure goes on to a seventh step SP7.

At the seventh step SP7, the gene counting section 44 detects every cell nucleus classified as a low counting precision cell nucleus. In addition, the gene counting section 44 also handles the low counting precision cell nucleus as a member to be actually visualize and verify. On top of that, the gene counting section 44 also determines the position of the low counting precision cell nucleus on the biological sample SPL. Finally, the gene counting section 44 terminates the procedure of the processing to count the number of genes at the end of the process carried out at the seventh step SP7.

If the fluorescent-image acquisition section 43 has generated a sample fluorescent image, the data recording section 45 produces sample data and records the data in the storage section 27. The sample data includes image information on the entire sample fluorescent image generated by the fluorescent-image acquisition section 43 or image information on a portion of the sample fluorescent image. However, the portion of the sample fluorescent image generated by the fluorescent-image acquisition section 43 can be used to reproduce the original sample fluorescent image.

In addition, the data recording section 45 also generates additional data and records the additional data in the storage section 27 by associating the additional data with the sample data described above. The additional data is data indicating average information representing averages computed by the gene counting section 44 at the sixth step SP6, position information representing positions found by the gene counting section 44 at the sixth step SP7 and identification information identifying the sample fluorescent image.

The identification information is information typically including the name of a person providing the biological sample SPL, the gender of the person, the age of the person and a date on which images of the biological sample SPL are taken. It is to be noted that the data recording section 45 notifies the operator of the biological-sample image acquisition apparatus 1 of a predetermined timing with which the identification information is to be entered by the operator. If the identification information may not be obtained when the data recording section 45 generates the sample data, the data recording section 45 issues a warning to urge the operator to promptly enter the identification information.

1-4: Effects and Others

In the configuration described above, every time the biological-sample image acquisition apparatus 1 moves sample members serving as the subject of an image acquisition process to the image acquisition range AR, the biological-sample image acquisition apparatus 1 also moves the movable stage 11 in the Z-axis direction (that is, the optical direction of the first objective lens 12A) in order to shift the focal point of the first objective lens 12A for the sample member in the thickness direction of the biological sample SPL.

In every operation carried out by the biological-sample image acquisition apparatus 1 to position the sample members serving as the subject of the image acquisition process at a location in an image acquisition range AR, the biological-sample image acquisition apparatus 1 exposes the image pickup device 30 to light during an exposure period which is started at a point of time the movement of the movable stage 11 in the Z-axis direction (that is, the optical direction of the first objective lens 12A) is commenced and terminated at a point of time the movement of the movable stage 11 in the Z-axis direction is ended. At the point of time the movement of the movable stage 11 in the Z-axis direction (that is, the optical direction of the first objective lens 12A) is ended, the biological-sample image acquisition apparatus 1 transfers fluorescent images of the sample members from the image pickup device 30 to the data processing section 20.

In the biological-sample image acquisition apparatus 1, a period in which the movable stage 11 is moved in the Z-axis direction (that is, the optical direction of the first objective lens 12A) is taken as an exposure period of a fluorescent image. Thus, the number of times to transfer fluorescent images of the sample members from the image pickup device 30 to the data processing section 20 is small in comparison with a configuration in which the focal point of an objective lens is moved from position to position at intervals determined in advance in the thickness direction of the biological sample to acquire the fluorescent images at each position. As a result, it is possible to reduce the processing load per biological sample and the amount of image data per biological sample.

In addition, since a period in which the focal point of the objective lens is being moved in the thickness direction is taken as the exposure period, even if a fluorescent marker (that is, a target marker) exists at any one of positions arranged in the thickness direction of the biological sample, the fluorescent marker is perceived as an equivalent luminescent spot.

Thus, in the biological-sample image acquisition apparatus 1, without regard to the depth of the focal point of the objective lens in use, it is possible to prevent a fluorescent marker from being dropped. As a result, it is possible to make the biological-sample image acquisition apparatus 1 capable of sustaining the precision of an operation to measure fluorescent markers at a certain level.

By the way, if a fluorescent image is acquired as an image for an exposure period in which the movable stage 11 is moved in the Z-axis direction (that is, the optical direction of the first objective lens 12A), a luminescent spot based on a fluorescent marker becomes an expanded luminescent spot as shown in the diagram of FIG. 7A. In this case, there is no problem in the counting operation itself. As is obvious from the diagrams of FIGS. 8A to 8C, however, it becomes difficult to determine the number of target markers each serving as the base of a luminescent spot SP in the case of two or more fluorescent markers FM placed at locations adjacent to each other or in the case of portions of two or more fluorescent markers FM overlapping each other with the biological sample SPL viewed in the thickness direction.

However, the biological-sample image acquisition apparatus 1 counts the number of luminescent spots each satisfying the condition requiring that the shape of the luminescent spot SP be circular to serve as a luminescent spot based on a fluorescent marker, excludes any cell nuclei each including a luminescent spot not satisfying the condition requiring that the shape of the luminescent spot SP be circular and computes an average of the luminescent spot counts each obtained for a cell nucleus as an average per cell nucleus.

Thus, even if each fluorescent image is acquired as an image for an exposure period in which the movable stage 11 is moved in the Z-axis direction (that is, the optical direction of the first objective lens 12A), the biological-sample image acquisition apparatus 1 is capable of accurately computing an average of the luminescent spot counts each obtained for a cell nucleus as an average per cell nucleus.

In addition, if radiation-subject markers each used for labeling a radiation-subject gene are utilized, the biological-sample image acquisition apparatus 1 is capable of setting the number of radiation-subject genes and the radiation-subject marker color. As described earlier, a radiation-subject gene is a gene to which light is to be radiated, a radiation-subject marker is a fluorescent marker for labeling a radiation-subject gene and a radiation-subject marker color is a color expressed by a radiation-subject marker.

In this case, the biological-sample image acquisition apparatus 1 excludes not only cell nuclei each including a luminescent spot not satisfying the condition requiring that the shape of the luminescent spot SP be circular, but also cell nuclei each having a radiation-subject marker count different from the set number of radiation-subject genes. Then, the biological-sample image acquisition apparatus 1 computes an average of the luminescent spot counts each obtained for a cell nucleus as an average per cell nucleus.

As explained earlier by referring to the diagrams of FIGS. 9A and 9B, in the case of a cell nucleus for which the number of markers each serving as the subject of light radiation is greater or smaller than the number of genes each serving as the subject of light radiation, it is quite within the bounds of possibility that the number of luminescent spots each based on one of target markers in cell nuclei is counted on the assumption that the target markers exist in one cell nucleus.

For the reason described above, the biological-sample image acquisition apparatus 1 excludes not only cell nuclei each including a luminescent spot not satisfying the condition requiring that the shape of the luminescent spot SP be circular, but also cell nuclei each having a radiation-subject marker count different from the set number of radiation-subject genes. Thus, with a higher degree of accuracy, the biological-sample image acquisition apparatus 1 is capable of accurately computing an average of the luminescent spot counts each obtained for a cell nucleus as an average per cell nucleus.

In addition, the biological-sample image acquisition apparatus 1 also generates position information representing the position of every cell nucleus which has been excluded in the process of computing an average of the luminescent spot counts each obtained for a cell nucleus as an average per cell nucleus. The biological-sample image acquisition apparatus 1 then records the position information in the storage section 27 by associating the position information with sample data.

Thus, the biological-sample image acquisition apparatus 1 is capable of immediately displaying every cell nucleus excluded in the process of computing an average of the luminescent spot counts each obtained for a cell nucleus as an average per cell nucleus on the display section 26. This capability of the biological-sample image acquisition apparatus 1 is useful from the following two points of view. One of the two points of view is the user friendliness of the biological-sample image acquisition apparatus 1 whereas the other point of view is the higher reliability of the precision of the operation to measure fluorescent marks.

In accordance with the configuration described above, at the end of an exposure period, a fluorescent image is acquired as an image for the exposure period in which the movable stage 11 is moved in the Z-axis direction (that is, the optical direction of the first objective lens 12A). As a result, it is possible to implement a biological-sample image acquisition apparatus 1 capable of sustaining the precision of the measurement of fluorescent marks at a certain level while reducing the processing load per biological sample and the amount of image data per biological sample.

2: Other Embodiments

As described above, the biological-sample image acquisition apparatus 1 exposes the image pickup device 30 to light during an exposure period which is started at a point of time the movement of the movable stage 11 in the Z-axis direction (that is, the optical direction of the first objective lens 12A) is commenced and terminated at a point of time the movement of the movable stage 11 in the Z-axis direction is ended. In such a configuration, due to a characteristic of the image pickup device 30, noises may be generated at a specific point in some cases. Since these fixed noises become a luminescent spot which has a shape approximately resembling a circle, it is not possible to distinguish the noises and a luminescent spot based on a target marker from each other. As a result, the precision of the counting operation carried out by the gene counting section 44 deteriorates in some cases.

In order to solve the problem described above, in place of a configuration for merely counting the number of luminescent spots each based on a target marker on a sample fluorescent image generated by the fluorescent-image acquisition section 43, it is possible to provide a configuration for counting the number of luminescent spots each based on a target marker on a noise-free sample fluorescent image which has been obtained by eliminating fixed noises from the sample fluorescent image generated by the fluorescent-image acquisition section 43.

To put it more concretely, a noise elimination section for eliminating fixed noises from a sample fluorescent image generated by the fluorescent-image acquisition section 43 is provided between the fluorescent-image acquisition section 43 and the gene counting section 44. When the fluorescent-image acquisition section 43 has generated a sample fluorescent image or a fluorescent image of a sample member serving as a subject of light radiation, the noise elimination section carries out a matching process to collate the sample fluorescent image or the fluorescent image of a sample member serving as a subject of light radiation with a pattern image of the fixed noises generated by the image pickup device 30. On the basis of a result of the matching process, the noise elimination section recognizes the position of the fixed noises and eliminates the fixed noises from the sample fluorescent image or the fluorescent image of a sample member serving as a subject of light radiation.

The pattern image is an image exposed to light during the exposure period without placing the biological sample SPL on the movable stage 11 in the dark-field speculum mode. The exposure period for exposing the pattern image to light without placing the biological sample SPL on the movable stage 11 in the dark-field speculum mode is the same period as the exposure period described earlier as a period to expose the biological sample SPL to light.

It is to be noted that a pattern image can be acquired by adoption of two typical techniques which are described as follows. In accordance with one of the techniques, prior to the start of every operation carried out to take a sample fluorescent image of the biological sample SPL, the pattern image is acquired in a calibration process. In accordance with the other technique, a pattern image is acquired from an external source connected to a network or from a storage medium with a timing determined in advance and the image is then stored in the storage section 27.

By employing the noise elimination section in such a configuration as described above, it is possible to prevent deterioration of the precision of the counting operation carried out by the gene counting section 44 to count the number of luminescent spots each based on a target marker to appear as a spot caused by adoption of the exposure period described earlier. As explained before, the exposure period is defined as a movement period which is started at a point of time the movement of the movable stage 11 in the Z-axis direction (that is, the optical direction of the first objective lens 12A) is commenced and terminated at a point of time the movement of the movable stage 11 in the Z-axis direction is ended.

In addition, in the case of the embodiment described above, the gene counting section 44 excludes low counting precision cell nuclei from all detected cell nuclei to result in remaining cell nuclei. Then, the gene counting section 44 computes an average of target-marker counts each obtained for one of the remaining cell nuclei as an average per cell nucleus. In this case, if the gene counting section 44 has determined earlier that the number of radiation-subject genes and/or a radiation-subject marker color have not been set, the low counting precision cell nuclei excluded from all the detected cell nuclei are low counting precision cell nuclei each classified as a cell nucleus in which there is a luminescent spot based on a target marker to appear as a luminescent spot not satisfying the condition requiring that the shape of the luminescent spot SP be circular. Thus, in this case, the gene counting section 44 does not select particular cell nuclei from all the detected cell nuclei in order to classify the selected particular cell nuclei as a special class of cell nuclei. A particular cell nucleus is a cell nucleus in which the number of markers each serving as the subject of light radiation is different from the number of genes each serving as the subject of light radiation as is the cases shown in the diagrams of FIGS. 9A and 9B. As a result, as explained earlier by referring to the diagrams of FIGS. 9A and 9B, it is difficult to determine whether or not the number of luminescent spots each based on a target marker in the cell nuclei is a result of a counting operation carried out by correctly assuming that the target markers exist in one cell nucleus.

Thus, in order to implement the function of the noise elimination section in particular, it is necessary to provide a noise elimination step typically between the first step SP1 and the second step SP2. The noise elimination step is carried out to classify probably abnormal cell nuclei as low counting precision cell nuclei and exclude the low counting precision cell nuclei from all detected cell nuclei to result in remaining cell nuclei. It is quite within the bounds of possibility that a probably abnormal cell nucleus is an abnormal cell nucleus. Thus, even if the gene counting section 44 has determined earlier that the number of radiation-subject genes and/or a radiation-subject marker color have not been set, the biological-sample image acquisition apparatus 1 is capable of accurately computing an average of target-marker counts each obtained for one of the remaining cell nuclei as an average per cell nucleus.

To put it more concretely, a cell nucleus satisfying neither a condition requiring that the circumferential edge of a cell nucleus be smooth nor a condition requiring that the shape of a cell nucleus be in a shape range ranging from a circular shape to an elliptical one is determined to be a probably abnormal cell nucleus and, thus, classified to pertain to the class of low counting precision cell nuclei.

The condition requiring that the circumferential edge of a cell nucleus be smooth may imply typically a case in which it is difficult to detect cell nuclei on corners at edges of an area including the following adjacent pixels. Each of the adjacent pixels corresponds to a nucleus marker color set as a color expressed by a cell nucleus and has a luminance not smaller than a threshold value determined in advance.

On the other hand, the condition requiring that the shape of a cell nucleus be in a shape range ranging from a circular shape to an elliptical one may imply typically a case in which the ratio of the major axis of an area described below to the minor axis of the area is not smaller than a threshold ratio determined in advance. The area includes adjacent pixels, each of which corresponds to a nucleus marker color set as a color expressed by a cell nucleus and has a luminance not smaller than a threshold value determined in advance.

In addition, in accordance with the embodiment described above, the biological-sample image acquisition apparatus 1 computes an average of target-marker counts each obtained for one of cell nuclei as an average per cell nucleus. However, the embodiment can be replaced by another embodiment described below or provided with the other embodiment as an additional embodiment. In accordance with the other embodiment, the biological-sample image acquisition apparatus computes the maximum or minimum value of target markers for each cell nucleus or the number of target markers in a sample fluorescent image.

On top of that, in accordance with the embodiment described above, genes are each used as a target on the biological sample SPL. However, a target on the biological sample SPL does not have to be a gene as is the case with this embodiment. For example, it is possible to provide another embodiment in which a target on the biological sample SPL is selected among a variety of molecules such as molecules of protein of a cell film channel, molecules of glycemic protein or molecules of a sugar chain.

In addition, in accordance with the embodiment described above, the number of target markers on a sample fluorescent image is counted. However, it is possible to provide another embodiment in which the target-marker count obtained as a result of counting the number of target markers on a sample fluorescent image is used as an indicator of the progression of a cancer. To put it more concretely, in this other embodiment, a cancer determination section is provided between the gene counting section 44 and the data recording section 45 to serve as a section for determining whether a result of a diagnosis carried out on a cancer patient is positive or negative.

The cancer determination section compares the average computed before for the cell nucleus with a threshold value used as a criterion for determining whether a result of a diagnosis carried out on a cancer patient is positive or negative. The average computed before for the cell nucleus is an average of target-marker counts each obtained for one of cell nuclei or an average of quotients each obtained by dividing the number of target markers for any particular one of cell nuclei by the number of radiation-subject markers for the same particular cell nucleus. In this way, the cancer determination section is capable of determining whether a result of a diagnosis carried out on a cancer patient is positive or negative with regard to the biological sample SPL. It is to be noted that, if the result of a diagnosis carried out on a cancer patient is positive, the progression of the cancer disease can be determined on the basis of the average of target-marker counts each obtained for one of cell nuclei or the average of quotients each obtained by dividing the number of target markers for any particular one of cell nuclei by the number of radiation-subject markers for the same particular cell nucleus.

On top of that, in accordance with the embodiment described above, after the biological-sample image acquisition apparatus 1 computes the number of luminescent spots each based on a target marker in a cell nucleus for every cell nucleus, the biological-sample image acquisition apparatus 1 classifies some cell nuclei as nuclei pertaining to the class of low counting precision cell nuclei each having target markers, the number of luminescent spots based on which may not be counted with a high degree of precision. In place of this embodiment, however, it is possible to provide another embodiment in which the biological-sample image acquisition apparatus 1 classifies some cell nuclei as nuclei pertaining to the class of low counting precision cell nuclei before the biological-sample image acquisition apparatus 1 computes the number of luminescent spots each based on a target marker in a cell nucleus for every cell nucleus.

In addition, in accordance with the embodiment described above, the movable stage 11 is moved in the Z-axis direction, that is, the optical direction of the first objective lens 12A which is fixed at a certain position. In place of this embodiment, however, it is possible to provide another embodiment in which the biological-sample image acquisition apparatus 1 firmly holds the movable stage 11 at a certain position and moves the first objective lens 12A in the Z-axis direction (that is, the optical direction of the first objective lens 12A).

In addition, it should be understood by those skilled in the art that a variety of modifications, combinations, sub-combinations and alterations may occur, depending on design requirements and other factors as far as they are within the scope of the appended claims or the equivalents thereof.

The embodiments can be applied to bio industries including gene experiments, manufacturing of medicines and observation of progress made by a patient.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A fluorescent-image acquisition apparatus comprising:
   an excitement-light source for radiating excitement light to a fluorescent marker on a biological sample;
   a dark-field radiation system;
   an objective lens for enlarging an image of a member of said biological sample;
   an image pickup device for forming said member image enlarged by said objective lens to appear as a fluorescent image of said member;
   a focal-point movement control means for moving the focal point of said objective lens in the thickness direction of said biological sample; and
   an image-pickup control means for exposing the image pickup device to light during an entire exposure period started when the focal-point movement control means commences moving the focal point of the objective lens in the thickness direction of the biological sample, and acquiring the member image enlarged by the objective lens to appear as the fluorescent image of the member from the pickup device at an end of the exposure period.

2. The fluorescent-image acquisition apparatus according to claim 1, said fluorescent-image acquisition apparatus further having noise elimination means for eliminating noises generated at a specific point on said fluorescent image due to exposure of said image pickup device from said fluorescent image by making use of a pattern image of said noises.

3. The fluorescent-image acquisition apparatus according to claim 1, said fluorescent-image acquisition apparatus further having computation means for:
   counting the number of luminescent spots each satisfying a circular-shape condition for every cell nucleus on said fluorescent image;
   excluding cell nuclei each including a luminescent spot not satisfying said circular-shape condition to result in remaining cell nuclei; and
   computing a value related to luminescent spots for each of said remaining cell nuclei.

4. The fluorescent-image acquisition apparatus according to claim 3, said fluorescent-image acquisition apparatus further having:
   image generation means for making use of a fluorescent image enlarged by said objective lens to appear as a fluorescent image of said member of said biological sample in order to generate a fluorescent image of said biological sample; and
   information recording means for recording information generated for said fluorescent image of said biological sample to serve as information showing the position of each of said cell nuclei excluded during computation processing carried out by said computation means by associating said recorded information with said fluorescent image of said biological sample.

5. The fluorescent-image acquisition apparatus according to claim 1, said fluorescent-image acquisition apparatus further having computation means for:
   counting the number of first luminescent spots each satisfying a circular-shape condition to serve as a luminescent spot based on said fluorescent marker for labeling a target molecule of said biological sample for every cell nucleus on said fluorescent image;
   counting the number of second luminescent spots each satisfying said circular-shape condition to serve as a luminescent spot based on said fluorescent marker for labeling a radiation-subject molecule of said biological sample for every cell nucleus on said fluorescent image;
   excluding cell nuclei each including said first and second luminescent spots each not satisfying said circular-shape condition and excluding cell nuclei each having a second-luminescent spot count different from a set number to result in remaining cell nuclei; and
   computing an average of quotients each obtained by dividing the number of said first luminescent spots each based on said fluorescent marker for labeling said target molecule for any particular one of remaining cell nuclei by the number of said second luminescent spots each based on said fluorescent marker for labeling said radiation-subject molecule for the same particular remaining cell nucleus.

6. The fluorescent-image acquisition apparatus according to claim 1, wherein the exposure period terminates when the moving of the focal point of the objective lens in the thickness direction of the biological sample is ended.

7. A fluorescent-image acquisition method comprising:
   carrying out dark-field radiation on a biological sample having a fluorescent marker appended to said biological sample;
   moving the focal point of an objective lens in the thickness direction of said biological sample having said fluorescent marker appended to said biological sample;
   exposing an image pickup device, on which an image enlarged by said objective lens to appear as a fluorescent image of a member of said biological sample is created, to light during an entire exposure period started when the focal point of the objective lens commences moving in the thickness direction of the biological sample; and
   acquiring the member image enlarged by the objective lens to appear as the fluorescent image of the member from the pickup device at an end of the exposure period.

8. The fluorescent-image acquisition method according to claim 7, wherein an end of the movement of the focal point of the objective lens triggers the end of the exposure period.

9. A non-transitory computer readable medium storing a program which when executed by a computer, causes the computer to:
   (a) carry out dark-field radiation on a biological sample having a fluorescent marker appended to said biological sample;
   (b) move the focal point of an objective lens in the thickness direction of said biological sample having said fluorescent marker appended to said biological sample;
   (c) expose an image pickup device, on which an image enlarged by said objective lens to appear as a fluorescent image of a member of said biological sample is created, to light during an entire exposure period started when the focal point of the objective lens commences moving in the thickness direction of the biological sample; and
   (d) acquire the member image enlarged by the objective lens to appear as the fluorescent image of the member from the pickup device at an end of the exposure period.

* * * * *